(12) United States Patent
Zimmon

(10) Patent No.: US 8,986,221 B2
(45) Date of Patent: Mar. 24, 2015

(54) APPARATUS AND METHODS FOR REMOVING SPRING BASED MULTIPLE BIOPSY SPECIMENS FROM MULTIPLE BIOPSY STORAGE CYLINDERS BEFORE AND AFTER BIOPSY FIXATION AND HISTOPATHOLOGICAL PROCESSING

(71) Applicant: David S. Zimmon, Port Washington, NY (US)

(72) Inventor: David S. Zimmon, Port Washington, NY (US)

( * ) Notice: Subject to any disclaimer, the term of this patent is extended or adjusted under 35 U.S.C. 154(b) by 99 days.

(21) Appl. No.: 13/966,926

(22) Filed: Aug. 14, 2013

(65) Prior Publication Data

US 2014/0052019 A1 Feb. 20, 2014

Related U.S. Application Data

(60) Provisional application No. 61/742,618, filed on Aug. 15, 2012.

(51) Int. Cl.
*A61B 10/02* (2006.01)
*A61B 10/00* (2006.01)
*A61B 10/06* (2006.01)

(52) U.S. Cl.
CPC .............. *A61B 10/02* (2013.01); *A61B 10/0096* (2013.01); *A61B 10/0266* (2013.01); *A61B 10/06* (2013.01); *A61B 2010/0225* (2013.01)
USPC ........................................................ 600/562

(58) Field of Classification Search
CPC ............... A61B 10/02; A61B 10/0096; A61B 10/0266; A61B 10/06; A61B 2010/0225
USPC .................................... 600/562–568; 606/167
See application file for complete search history.

(56) References Cited

U.S. PATENT DOCUMENTS

| | | |
|---|---|---|
| 5,685,320 A | 11/1997 | Zimmon et al. |
| 5,782,747 A | 7/1998 | Zimmon |
| 6,071,248 A | 6/2000 | Zimmon |
| 7,445,603 B2 | 11/2008 | Zimmon |

*Primary Examiner* — Brian Szmal
(74) *Attorney, Agent, or Firm* — Collard & Roe, P.C.

(57) ABSTRACT

An apparatus for removing biopsies from spring based multiple biopsy storage cylinders for analysis. The storage cylinders and spring based biopsy mechanism permit 360 degree biopsy mechanism rotation and increase the number and diameter of biopsies stored. Additional storage cylinder improvements allow closed storage cylinder opening for removing internal plastic cylinders or biopsies before fixing, thereby leaving the same multiple biopsy instrument available for additional biopsies on the same patient. The improvements allow for removing the surrounding biopsy mechanism and biopsies from closed storage cylinders after actuator removal and histopathological processing of biopsies to paraffin embedding. Additionally apparatuses, tools and methods are described for simultaneously separating numerous actuators from storage cylinders and removing numerous paraffin embedded biopsies from storage cylinders and surrounding biopsy mechanisms for histopathological slide fabrication.

19 Claims, 5 Drawing Sheets

APPARATUS AND METHODS FOR REMOVING SPRING BASED MULTIPLE BIOPSY SPECIMENS FROM MULTIPLE BIOPSY STORAGE CYLINDERS BEFORE AND AFTER BIOPSY FIXATION AND HISTOPATHOLOGICAL PROCESSING

CROSS-REFERENCE TO RELATED APPLICATIONS

This application claims priority under 35 USC 119(e) of U.S. Provisional Application No. 61/742,618, filed on Aug. 15, 2012, the disclosure of which his hereby incorporated by reference.

BACKGROUND OF THE INVENTION

Field of the Invention

The present invention relates to removing, collecting, fixing and processing of biopsies from spring based multiple biopsy instruments for analysis by histopathological, chemical, biological, genetic or physical methods. Biopsies are minute pieces of fragile tissue that are difficult to handle during biopsy removing, collecting, fixing and histopathological processing. A spring based multiple biopsy device solves these problems by removing, serially collecting, orienting and storing biopsies in acquisition order within a closed plastic or metal storage cylinder for in situ fixing and histopathological processing. After removing the long actuator shaft and handle, spring based multiple biopsy closed storage cylinders holding biopsies require opening during processing and slide fabricating for microscopic examination or other analyses. Fixed biopsies for microwave processing or unfixed biopsies for frozen section examining require separating an internal plastic biopsy collecting cylinder from the surrounding biopsy mechanism and external storage cylinder. After in situ histopathological processing, minute biopsies embedded in paraffin need removing from the surrounding biopsy mechanism and storage cylinder. An efficient method for performing these operations on numerous multiple biopsy devices sent to the pathology laboratory after removing the long actuator shaft and handle is needed.

U.S. Pat. Nos. 5,685,320, 5,782,747, 6,071,248 and 7,445,603 to Zimmon, herein incorporated by reference, describe a spring based multi-purpose medical instrument and a spring based multiple biopsy device for serial collection, storage and processing of biopsies in situ that cuts and captures a series of biopsies in a single pass to the biopsy site for fixing and processing in situ and a removable distal internal cassette for in situ fixation and biopsy processing with serial collection and storage of biopsy specimens.

Biopsies are collected, oriented and stored in acquisition order inside a closed, perforated plastic or metal storage cylinder surrounded by the biopsy mechanism or in a perforated removable internal plastic cylinder. The storage cylinder is closed by withdrawing the biopsy mechanism into the storage cylinder after completing the biopsy series. After retrieving from the biopsy access path, the closed storage cylinder is separated from the biopsy device shaft and placed in a container. Closing the storage cylinder maintains biopsy orientation and acquisition order, prevents specimen loss and contamination during passage through the access path and protects staff from the sharp biopsy jaws and human material while handling the instrument.

In the pathology laboratory, the closed storage cylinder is immersed in a series of solvents and permeated with hot paraffin contacting the biopsies through cylinder perforations. After cooling, paraffin embedded biopsies need removing from the surrounding storage cylinder and biopsy mechanism. The fragile 2 mm diameter paraffin embedded biopsies column must remain intact and straight for mounting, microtome slicing and slide fabricating to maintain biopsy orientation and acquisition order and identify the biopsy site of each biopsy on the microscope slide. Opening the storage cylinder and removing the fragile paraffin embedded column of biopsies from the storage cylinder and biopsy mechanism without damage is difficult. Mounting numerous serial microtome sections of oriented biopsies in acquisition order on a single glass slide reduces the number of slides fabricated and cost. These slow manual, laborious and costly procedures need improvement.

In U.S. Pat. No. 7,445,603 by Zimmon, herein incorporated by reference, the spring based multiple biopsy captures biopsies in a removable perforated plastic cylinder held within the biopsy mechanism and storage cylinder. The closed storage cylinder needs opening for removing the removable plastic cylinder for rapid diagnosis by frozen section or microwave processing that are incompatible with the metal biopsy mechanism and storage cylinder.

The internal plastic storage cylinder held within the biopsy mechanism is 2 mm in diameter. In the operating room, removing the 2 mm plastic cylinder from the multiple biopsy device requires two operators. One operator, holding the long shaft and handle, advances the actuator and opening the biopsy device exposing the plastic cylinder. The second operator, holding the storage cylinder, removes the plastic cylinder. These actions risk damaging the storage cylinder and biopsies and exposing staff to the sharp jaws and infectious material. The operative procedure is delayed and anesthesia prolonged with increased patient risk and cost. This manual task is better done at a pathology laboratory bench. To this purpose, the storage cylinder with the removable plastic cylinder is separated from the actuator shaft for opening in the pathology laboratory. An efficient method for opening storage cylinders and removing the contents in the pathology laboratory is needed.

The prior art has made multiple biopsy with biopsy serial collection, orientation and storage in acquisition order for in situ fixation and processing safe and efficient. A need for improvement remains

SUMMARY OF THE INVENTION

It is therefore an object of the present invention to provide an apparatus for removing multiple biopsies from storage cylinders for analysis by chemical, biological, genetic or physical methods. The invention improves the spring based multiple biopsy storage cylinder and biopsy mechanism increasing the number and size of biopsies collected in a storage cylinder. Storing more biopsies of larger diameter increases the quantity of diagnostic tissue collected in each biopsy pass to the target tissue. Greater tissue volume and mucosal area (biopsy numbers times diameter) of collected tissue increases the diagnostic value of each biopsy pass.

One embodiment of the invention is an improved spring based multiple biopsy device biopsy mechanism for serial collection, storage and processing of biopsies as described in U.S. Pat. No. 6,071,248 to Zimmon, herein incorporated by reference, wherein the apex of the spring jaw is changed to a flat perforated connecting disc, thereby increasing the biopsy holding volume, biopsy diameter and the number of biopsies in a storage cylinder and the internal biopsy mechanism. Removing biopsies from the perforated storage cylinder is improved by adding a proximal slot, and a distal positioning notch at the storage cylinder edge 180 degrees opposite the slot. The proximal storage cylinder slot exposes the space between the actuator wire and the biopsy mechanism disc back. After removing actuator shaft and handle, a pin inserted in the slot pushing distally moves the disc back and biopsy mechanism out of the closed storage cylinder, exposing the contents. By grasping the jaws, the biopsy mechanism and contents can be extracted from the storage cylinder. Irrigating through the slot and perforated biopsy mechanism disc after opening the jaws allows removing biopsy batches from the storage cylinder and reuse of the washed device on the same patient. The lumen narrowing inclined biopsy mechanism guide ramp of the Spring Based Multi-Purpose Medical Instrument, as described in U.S. Pat. No. 5,782,747 to Zimmon, herein incorporated by reference, is improved to a circumferential jaw guide cam biopsy mechanism, maximizing the storage cylinder holding volume, permitting 360 degree biopsy mechanism rotation and inserting or extracting of a larger removable internal plastic biopsy collecting cylinder. The circumferential guide ramp wide open unobstructed lumen increases the number and diameter of biopsies collected within the storage cylinder and facilitates removing a paraffin embedded biopsy column from the storage cylinder. Similarly, opening storage cylinders and removing biopsies after separating the spring based multiple biopsy actuator shaft and operating handle from the storage cylinder is facilitated.

Another embodiment of this invention is a heated storage cylinder opening apparatus with a hinged cover and attached guillotine for uniformly separating spring based multiple biopsy storage cylinders from their shafts. A platform groove with a constriction at the storage cylinder junction with the narrower shaft for each length of storage cylinder positions the shaft for guillotine shaft removal. A post at the edge of each platform groove docks into a storage cylinder edge notch, fixing the storage cylinder opening slot vertically and horizontally. A hinged movable bar with a series of biopsy mechanism removing pins extending through cover openings are positioned to enter each closed storage cylinder slot between the actuator wire and the biopsy mechanism flat back disc. Advancing the movable bar and removing the pins opens the ganged closed multiple biopsy cylinders in a single action.

After collecting a spring based multiple biopsy series and before removing from the biopsy site(s), the storage cylinder is closed by retracting the sharp jaws and biopsy mechanism into the storage cylinder. After removing most of the actuator with the long shaft, biopsies in the closed storage cylinder are immersed in preserving fixative. In the pathology laboratory, individual storage cylinders are opened with a pin placed in the storage cylinder slot and pushed distally, moving the jaws out of the cylinder for grasping and pulling the biopsy mechanism surrounding the biopsies out of the storage cylinder.

For opening numerous storage cylinders, the storage cylinders and shaft stub are placed in the removing platform grooves with the storage cylinder notch in the platform end post. Closing the hinged platform cover and guillotine separates the shaft stubs, leaving short, sharply cut shaft stubs and actuators and fixing storage cylinder positions. The movable opening pin bar is closed, passing the pins through platform cover openings into storage cylinder slots. Advancing the sliding pin bar moves the pins forward in the storage cylinder slots forcing the biopsy mechanism disc back and jaws distally out of the storage cylinder for grasping and removing internal plastic storage cylinders or biopsy mechanisms surrounding biopsies.

The removing platform is heated, softening paraffin for removing biopsies after processing to paraffin embedding. The removing platform has a tray with spaces for labeled processing or mounting cassettes in front of each groove to receive the biopsies from storage cylinders and maintain identification.

The invention also includes biopsy removal tools for grasping and pulling sharp jaws and biopsy mechanism out of the storage cylinder, for spreading the sharp jaws and metal biopsy mechanism surrounding the biopsies, far separating the biopsy column from the biopsy mechanism, and for grasping and surrounding the heated soft column of paraffin embedded biopsies between the spread arms of the biopsy mechanism and straightening the biopsy column before cooling, wrapping, mounting and microtome slicing. The heated platform maintains storage cylinders with paraffin embedded biopsies at a temperature to soften the paraffin, facilitating removing from the biopsy mechanism. Softening the paraffin prevents disruption of the paraffin embedded biopsy column during removing and allows straightening of the 2 mm diameter column.

One embodiment for removing spring based multiple biopsies by irrigating is to open the slot by activating the biopsy mechanism. Irrigating with a needle placed through the storage cylinder slot in the space behind the biopsy mechanism forces fluid through the biopsy mechanism, entraining the biopsies to pass out between the open jaws into a receptacle. This can be done in the operating room without removing the spring based multiple biopsy shaft and handle. After collecting the biopsies, the spring based multiple biopsy device is washed and available for additional biopsies.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
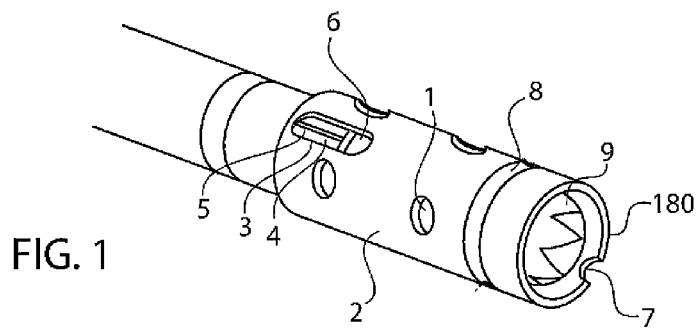
FIG. 1 shows a spring based multiple biopsy device according to the invention before removing from the biopsy site. The biopsy series is held in the perforated storage cylinder in acquisition order surrounded by the biopsy mechanism spring arms and jaws closed by the circumferential cam guide during retracting into the storage cylinder. After removing the long shaft, the biopsies are ready for immersing in preserving fixative and in situ histopathological processing. Storage cylinder perforations allow biopsy permeation during fixing and processing.

FIG. 1 shows a closed perforated multiple biopsy storage cylinder 2 according to the invention with a slot 3 positioned to allow access to the space 4 between the actuator 5 and the biopsy mechanism flat disc back 6. A positioning notch 7 at the storage cylinder edge 180 degrees opposite the slot 5 fixes the storage cylinder slot longitudinally and vertically. A circumferential cam guide 8 projects into the interior of storage cylinder 2, with a semicircular or oval cross-section, extending around the entire circumference of cylinder 2. This can be made by stamping cam guide 8 into cylinder 2 so that cylinder 2 is indented all around the circumference, as shown in the drawings. Retracting the actuator 5 closes the storage cylinder 2 when the circumferential cam guide 8 compresses the jaws 9 as they are pulled into the cylinder. Multiple biopsy devices are closed when passing to or retrieving from the biopsy site. Collected biopsies in the closed storage cylinder 2 are held in acquisition order and protected from contamination or loss by the closed jaws.

Figure 2:
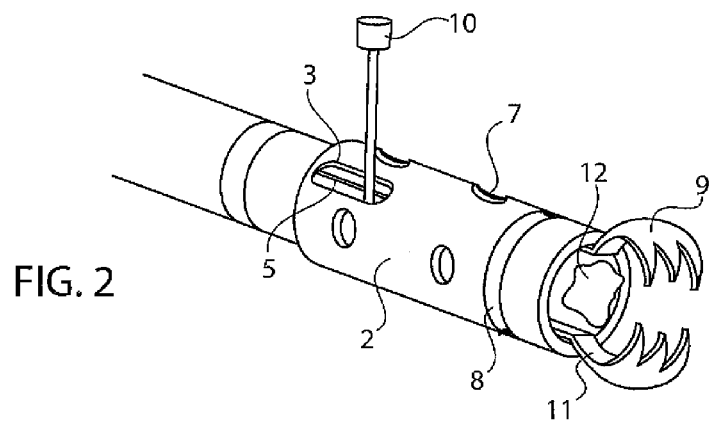
FIG. 2 shows an opened perforated multiple biopsy storage cylinder with in situ histopathologically processed paraffin embedded biopsies and a cylinder slot pushing pin or irrigating needle according to the invention. After moving the jaws and biopsy mechanism out of the storage cylinder with a pin pushing on biopsy mechanism disc back, the jaws and biopsy mechanism surrounding the contents are exposed ready for grasping and removing. Alternatively, after a biopsy series, the multiple biopsy can be removed from the biopsy site and opened by activating the biopsy mechanism. Irrigating through the cylinder slot behind the biopsy mechanism and expelling the stored biopsies through the open jaws, allows collecting numerous biopsy batches with the same instrument.

FIG. 2 shows a spring based multiple biopsy device storage cylinder 2 according to the invention after completing a biopsy, reopened for another biopsy by advancing the actuator. The preceding biopsy 12 is within the biopsy mechanism 11. On reaching the biopsy site, advancing the actuator 5 pushes the jaws 9 and open biased spring biopsy mechanism 11 out of the storage cylinder 2. On passing the cam guide 8, the jaws 9 spring open. The operator pushes the jaws into the tissue surrounding the biopsy 12. Retracting the actuator draws the jaws 9 over the cam guide 8 closing the jaws around the biopsy, cutting the biopsy from surrounding tissue and drawing the biopsy 12 into the storage cylinder 2 between the spring arms 13. Each subsequent biopsy 12 pushes the preceding biopsy deeper into the storage cylinder 2 until the storage cylinder is filled. After filling, the storage cylinder 2 is closed by retracting the actuator 5, which closes the storage cylinder 2 with the closed jaws for retrieval from the biopsy site. The long actuator 5 and handle are removed and the closed storage cylinder with biopsies 12 is immersed in fixative and sent to pathology for histopathological processing. In pathology to open the storage cylinder 2 after processing, a pin 10 in the slot 3 pushed distally (toward the jaws 9) moves the open biased spring based biopsy mechanism 11 and jaws 9 beyond the circumferential cam guide 8 out of the storage cylinder 2 where the jaws 9 spring open. Pulling the jaws 9 extracts the biopsy mechanism with biopsies or plastic cylinder (not shown) out of the storage cylinder. To remove biopsies before processing, irrigating fluid injected into the slot 4 with a needle (not shown) passes through the biopsy mechanism perforated back disc between the biopsy mechanism arms and open jaws 9, entraining the biopsies 12 into a receptacle (not shown).

Figure 3:
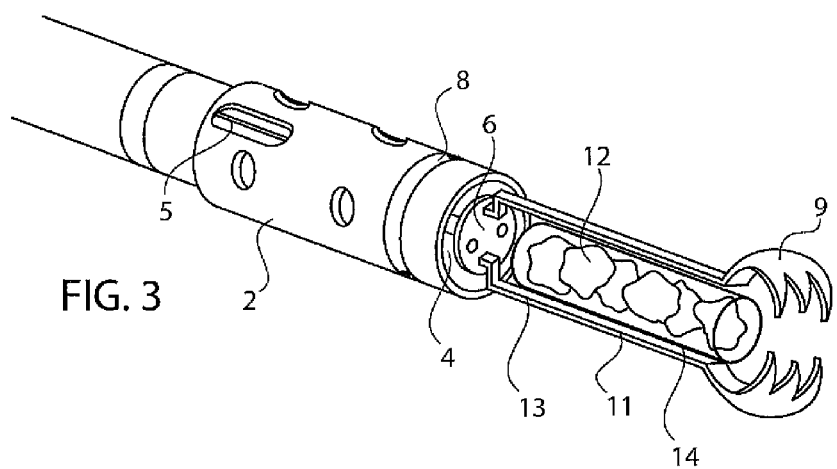
FIG. 3 shows an exploded view of a spring based multiple biopsy device with removable plastic storage cylinder holding biopsies according to the invention. After pushing the biopsy mechanism out of the storage cylinder with a pin in the storage cylinder slot and pulling the jaws to remove the plastic cylinder with surrounding biopsy mechanism.

FIG. 3 shows a view of a multiple biopsy storage cylinder 2 according to the invention with removable plastic storage cylinder 14 holding collected biopsies 12 between the biopsy mechanism spring arms 13 and jaws 9. The circumferential cam guide 8 allows 360 degree rotation of the biopsy mechanism and without limiting the diameter of the biopsy 12. The flat disc back 6 connecting the spring arms 13 is perforated for passing irrigating fluid injected through the slot 3 into the space 4 between the biopsy mechanism 11 and actuator 5 out of the open jaws 9, entraining biopsies 12 out of the storage cylinder 2. After pushing the biopsy mechanism 11 out of the storage cylinder 2 with a pushing pin (not shown), removable plastic storage cylinders 14 surrounding multiple biopsies 11 or paraffin embedded biopsies within the biopsy mechanism are exposed for extraction by grasping the exposed jaws 9 and pulling the entire biopsy mechanism 11 out of the storage cylinder 2.

Figure 4:
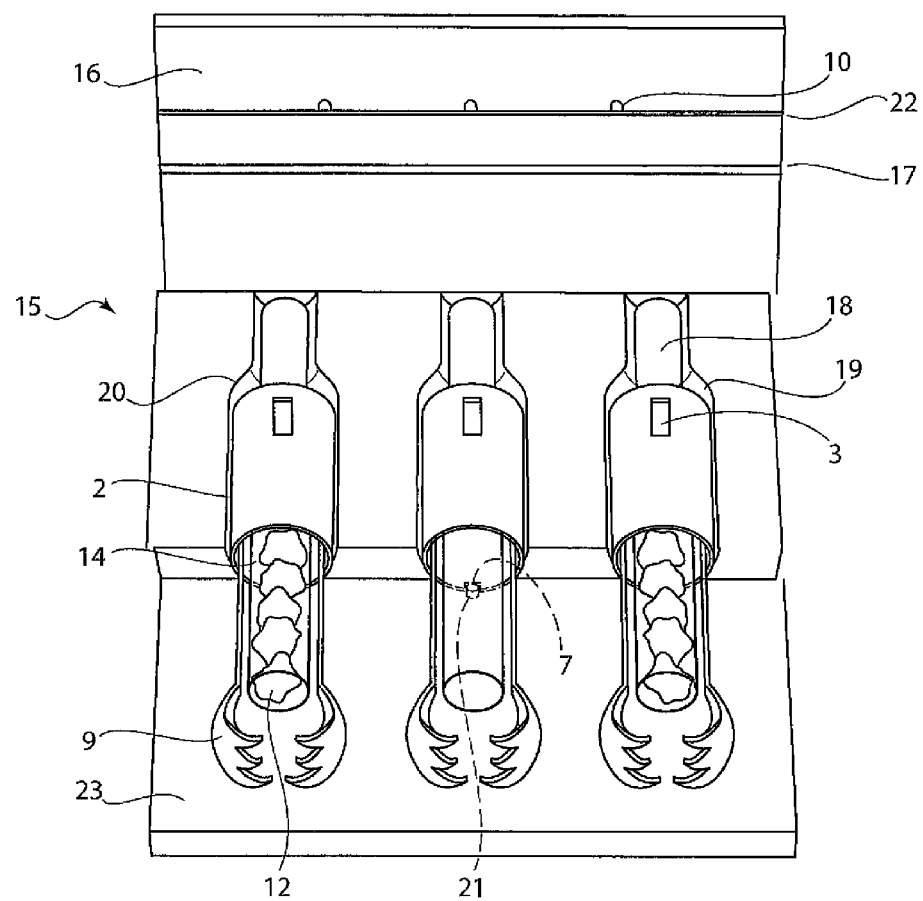
FIG. 4 shows a heated ganged storage cylinder opening platform en face according to the invention with a hinged cover containing shaft removing guillotine and storage cylinder opening pins bar. The platform has storage cylinder and shaft positioning grooves and platform edge docking pins to lock edge notched storage cylinders vertically and horizontally. Closing the hinged platform cover guillotines the shafts forcing cylinder opening pins through the cylinder slots into the space between the actuator and biopsy mechanism back. Advancing the pushing pin bar pushes the open biased spring biopsy mechanism beyond the circumferential cam guide. The open biased spring biopsy mechanism opens the jaws exposing the storage cylinder contents for removing. For identification, collection trays with cassettes are placed below each storage cylinder.
Figure 5:
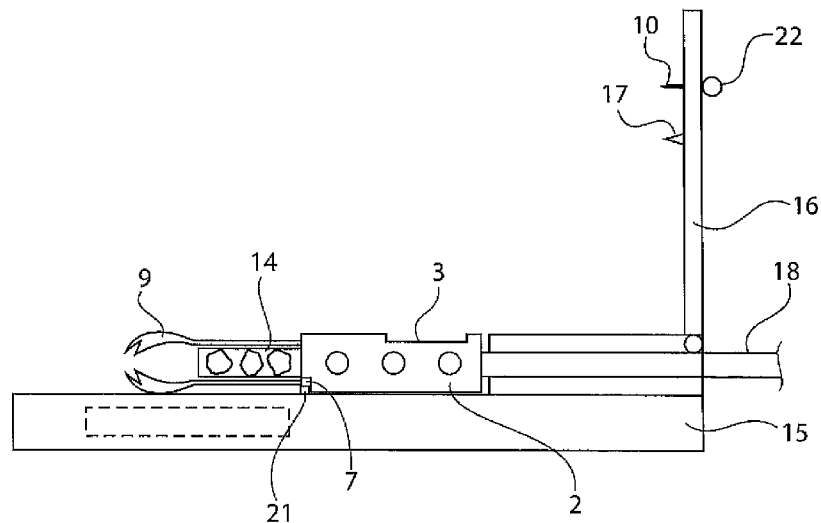
FIGS. 5 and 6 show lateral and enlarged views, respectively, of the heated storage cylinder opening platform according to the invention with hinged cover open after separating the shaft by guillotine and storage cylinder opening by pin bar. Storage cylinder and shaft positioning grooves and platform edge docking pins lock edge notched storage cylinders vertically and horizontally. The biopsy mechanism jaws and removable perforated plastic cylinder extend over the biopsy collection tray for removing from storage cylinders.
Figure 6:
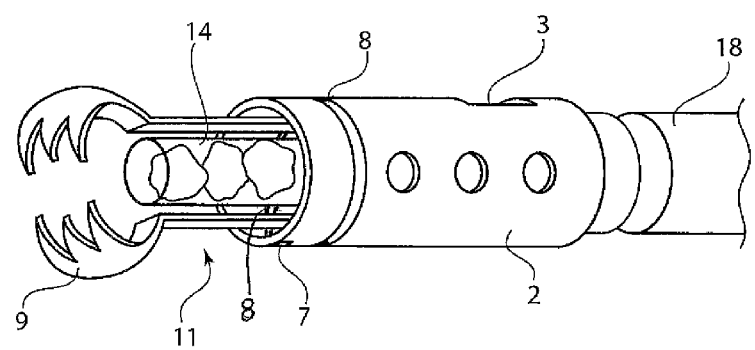

FIGS. 4-6 show a heated biopsy removal platform 15 according to the invention with hinged cover 16 holding a guillotine 17 for simultaneously separating actuator shafts 18 from numerous multiple biopsy storage cylinders 2 and removing numerous biopsy mechanisms 11 surrounding biopsies 12 or plastic removable storage cylinders 14 holding biopsies. Grooves 19 in the platform 15 for each storage cylinder length have a constriction 20 at the junction of the storage cylinders 2, and narrower shafts 18 that position the storage cylinders at the end of the biopsy removal platform grooves 19, align the long shaft 18 for separating the shafts by guillotine 17 and dock the storage cylinder edge notches 7 in the platform edge posts 21, fixing the cylinder opening slots 3 vertically and horizontally. The hinged platform cover 16 has a movable bar 22 with pushing pins 10 placed to dock in the storage cylinder opening slots 3 fixed in position by the platform end positioning posts 21 in the storage cylinder edge notches 7. Closing the platform cover 16 separates the storage cylinders shafts 18 by guillotine 17 and holds cylinders 2 stationary with platform edge posts in storage cylinder notches opening pin docking in cylinder slots. The storage cylinder 2 is opened by pushing the movable opening pin bar 22 distally, forcing the biopsy mechanism 11 out of the cylinder 2 where the jaws 9 are grasped and biopsy mechanism 11 withdrawn. The storage cylinder platform 15 has trays 23 for labeled cassettes (not shown) under each storage cylinder groove 19 for receiving the biopsies and maintaining identification.

Figure 7:
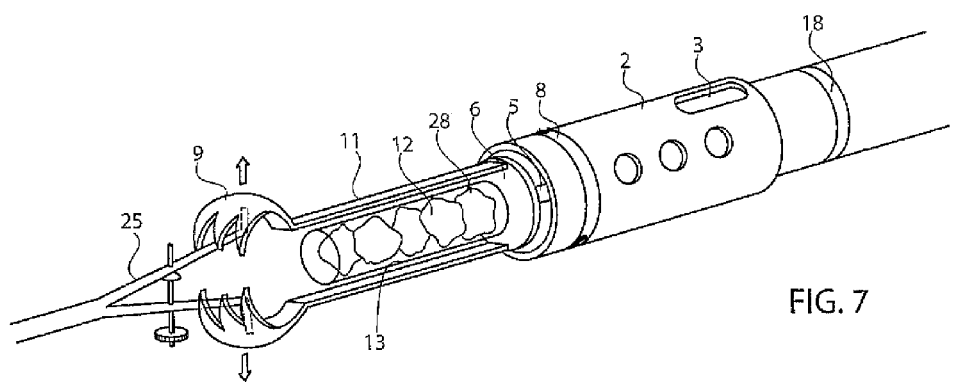
FIG. 7 shows the jaw grasping tool according to the invention for grasping and extracting the sharp jaws and biopsy mechanism surrounding processed paraffin embedded biopsies from the storage cylinders.

FIG. 7 shows a jaw grasping tool 25 according to the invention for extracting the metal biopsy mechanism 11 with a disc back 6 connecting the spring arms 13 and actuator 5 surrounding the fragile paraffin embedded biopsy column 28 from the storage cylinder 2. The tool 25 grasps the jaws 9 by their inner sharp edges to avoid compressing the soft heated paraffin embedded biopsies 12 during extracting from the storage cylinder 2. Then the tool spreads and bends the jaws 9 and spring biopsy mechanism 11 away from the paraffin embedded biopsy column 12.

Figure 8:
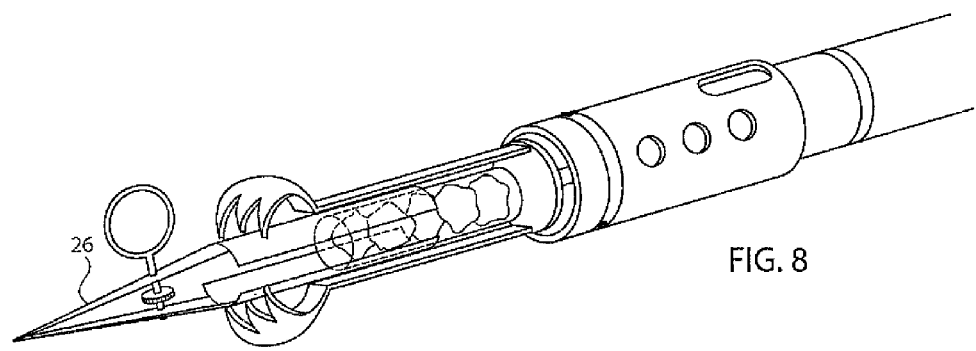
FIG. 8 shows the jaw grasping spring based arm spreading tool according to the invention for separating the paraffin embedded specimen column from the spring biopsy mechanism.

FIG. 8 shows a paraffin embedded biopsy column grasping tool 26 according to the invention after inserting between the bent spring arms 13 of the biopsy mechanism 11 and grasping the paraffin embedded biopsy column for removing from the biopsy mechanism 11.

Figure 9:
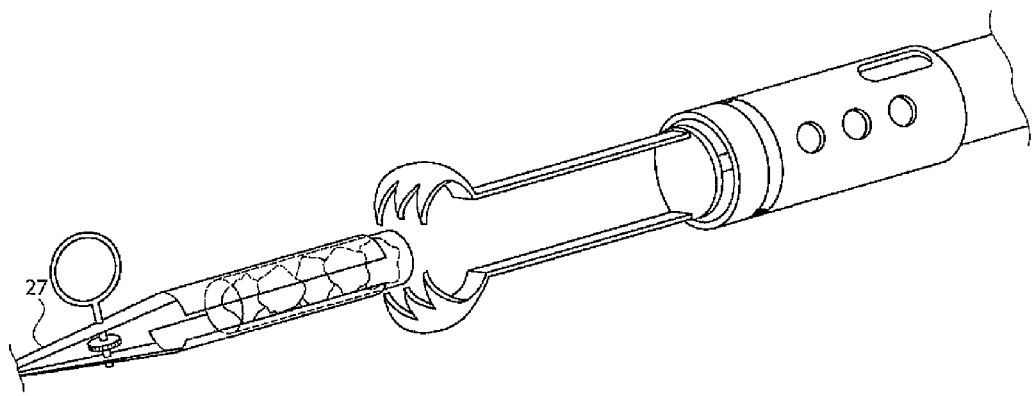
FIG. 9 shows the paraffin embedded biopsy column straightening tool according to the invention for grasping, removing from the storage cylinder and straightening the column for mounting and microtome slicing.

FIG. 9 shows a paraffin embedded specimen column surrounding and straightening tool 27 for removing any column distortion occurring during removal from the storage cylinder 2 and biopsy mechanism 11.

Accordingly, while only a few embodiments have been shown and described, it is it is obvious that many changes and modifications may be made thereunto without departing from the spirit and scope of the invention.

What is claimed is:

1. An apparatus for performing a medical procedure, comprising:
    an elongated rigid or flexible member having an aperture extending longitudinally therethrough, said member having a proximal end and an opposite distal end;
    an actuator positioned within said aperture, said actuator having a proximal end and a opposite distal end;
    a spring based biopsy mechanism with spring arms with jaws joined proximally by a perforated flat metal disc, said flat metal disc being connected to said distal end of said actuator, said jaws being deployable remotely for performing a medical procedure;
wherein said biopsy mechanism is positioned within a perforated metal or plastic biopsy storage cylinder configured for collection of multiple biopsies in the order of acquisition in a single pass to a biopsy site; and
wherein said perforated metal or plastic storage cylinder is attached to said flexible or rigid elongated member.

2. The apparatus of claim 1, wherein said perforated metal or plastic multiple biopsy storage cylinder has a slot positioned to expose a space between said actuator and said perforated flat metal disc connecting said spring based biopsy mechanism.

3. The apparatus of claim 2, wherein said perforated metal or plastic multiple biopsy storage cylinder has a positioning notch at a distal edge 180 degrees opposite said slot.

4. The apparatus of claim 1, wherein said perforated metal or plastic multiple biopsy storage cylinder has a circumferential cam ramp guide placed in a wall of the storage cylinder, allowing 360 degree rotation of said biopsy mechanism and said jaws when said actuator is rotated.

5. The apparatus of claim 1, wherein said circumferential cam ramp guide controls the opening and closing of the spring jaws.

6. The apparatus of claim 1, wherein said jaws hold said biopsies within said storage cylinder in acquisition order and limit contamination of said biopsies within said closed storage cylinder.

7. The apparatus of claim 1, further comprising a perforated plastic internal storage cylinder inserted within said plastic or metal storage cylinder between said biopsy mechanism and said jaws.

8. The apparatus of claim 7, wherein said biopsy mechanism holds the perforated removable plastic internal storage cylinder within said storage cylinder during withdrawing from a biopsy site.

9. The apparatus of claim 7, wherein said perforated removable plastic internal storage cylinder is removable from said storage cylinder for processing and analysis of said biopsies.

10. The apparatus of claim 1, wherein the spring based biopsy mechanism is reusable.

11. The apparatus of claim 9, wherein pushing the biopsy mechanism distally moves said biopsy mechanism out of said storage cylinder opening, for grasping and removing said removable plastic internal storage cylinder for processing and analysis of said biopsies.

12. The apparatus of claim 3, further comprising means for irrigating through said storage cylinder slot for removing said biopsies.

13. The apparatus of claim 1, further comprising a tool adapted to grasp said jaws and extract said biopsy mechanism from said storage cylinder and spread said biopsy mechanism spring arms.

14. The apparatus of claim 13, further comprising an additional tool adapted to grasp a paraffin embedded specimen column from between said spring arms and remove said paraffin embedded specimen column from said biopsy mechanism.

15. The apparatus of claim 14, further comprising a further tool adapted to surround, grasp, straighten and cool said paraffin embedded specimen column after removing from said biopsy mechanism.

16. The apparatus of claim 15, wherein the column straightening tool is adapted to surround the paraffin specimen column for straightening and remove any column irregularities in preparation for mounting and microtome slicing.

17. A system for collecting and storing biopsies, comprising;
    a heated platform;
    a plurality of apparatuses according to claim 3 disposed on the platform;
    a plurality of grooves in the platform for holding each apparatus, each groove having a portion for holding the storage cylinders at a platform edge, and a narrowed portion for holding the elongated rigid or flexible member;
    a positioning post at the platform edge of each groove sized to dock into the notch of each storage cylinder, fixing the storage cylinder horizontally and vertically;
    a hinged platform cover connected to the platform at an opposite platform edge, the platform cover holding a guillotine corresponding to each groove, the guillotine entering each groove in the platform for separating said elongated rigid or flexible members from said storage cylinders when closing the hinged cover;
    a movable bar with pins extending through said platform cover openings positioned for entering the slots in each storage cylinder on closing the hinged cover; and a tray holding processing or analysis cassettes at the platform edge under the grooves for receiving contents of said storage cylinders.

18. The system of claim 17, wherein the platform grooves and storage cylinder slots are adapted to fix said storage cylinders vertically and horizontally.

19. The system of claim 17, wherein moving said platform cover pin connecting bar distally pushes said biopsy mechanism and jaws out of said storage cylinder and opens said spring jaws.

* * * * *